United States Patent
King et al.

(10) Patent No.: US 9,353,044 B2
(45) Date of Patent: May 31, 2016

(54) REDUCTIVE AMINATION OF DIETHANOLAMINE AND RESULTING PRODUCT MIXTURE

(71) Applicant: DOW Global Technologies LLC, Midland, MI (US)

(72) Inventors: Stephen W. King, League City, TX (US); Sadeka Onam, Midland, MI (US); Thomas Z. Srnak, Arlington Heights, IL (US)

(73) Assignee: Dow Global Technologies, LLC, Midland, MI (US)

( * ) Notice: Subject to any disclaimer, the term of this patent is extended or adjusted under 35 U.S.C. 154(b) by 13 days.

(21) Appl. No.: 14/369,427

(22) PCT Filed: Nov. 14, 2012

(86) PCT No.: PCT/US2012/064966
§ 371 (c)(1),
(2) Date: Jun. 27, 2014

(87) PCT Pub. No.: WO2013/095810
PCT Pub. Date: Jun. 27, 2013

(65) Prior Publication Data
US 2014/0371452 A1 Dec. 18, 2014

Related U.S. Application Data

(60) Provisional application No. 61/579,508, filed on Dec. 22, 2011.

(51) Int. Cl.
| | | |
|---|---|---|
| *C07D 295/00* | (2006.01) | |
| *C07C 213/02* | (2006.01) | |
| *C07D 295/023* | (2006.01) | |
| *B01J 21/12* | (2006.01) | |
| *B01J 23/889* | (2006.01) | |
| *B01J 23/89* | (2006.01) | |
| *B01J 37/02* | (2006.01) | |

(52) U.S. Cl.
CPC ............. *C07C 213/02* (2013.01); *B01J 21/12* (2013.01); *B01J 23/8896* (2013.01); *B01J 23/89* (2013.01); *B01J 37/0201* (2013.01); *C07D 295/00* (2013.01); *C07D 295/023* (2013.01); *C07C 2529/89* (2013.01)

(58) Field of Classification Search
CPC ..................................................... C07D 295/00
See application file for complete search history.

(56) References Cited

U.S. PATENT DOCUMENTS

| | | | |
|---|---|---|---|
| 3,682,919 A | 8/1972 | Johansson et al. | |
| 3,849,262 A | 11/1974 | Cocuzza | |
| 4,123,462 A | 10/1978 | Best | |
| 4,400,539 A * | 8/1983 | Gibson et al. | 564/480 |
| 4,701,434 A | 10/1987 | Koll | |
| 4,863,890 A | 9/1989 | Koll | |
| 5,851,948 A | 12/1998 | Chuang et al. | |
| 7,279,602 B2 | 10/2007 | Reif et al. | |
| 2008/0003131 A1 | 1/2008 | Bauer et al. | |
| 2010/0087684 A1 | 4/2010 | Do et al. | |

FOREIGN PATENT DOCUMENTS

| | | |
|---|---|---|
| EP | 1249440 | 10/2002 |
| WO | WO 2006/053342 | 5/2006 |

OTHER PUBLICATIONS

*Encyclopedia of Chemical Technology*, vol. 2, 5th Edition, Kirk-Othmer, p. 221 et seq., 1992.
Tanabe et al. "*A New Hypothesis Regarding the Surface Acidity of Binary Metal Oxides*" Bulletin of the Chemical Society of Japan, 47(5):1064-1066, 1974.
Komiyama et al. "Concentration Profiles in Impregnation of Porous Catalysts: Nickel on Alumina," J. of Catalysis 63, 35-52, 1980.
G.A. Klinger et al., "Hydroamination of Diethanolamine and Its N-Alkyl Derivatives Inthe Presence of Heterogeneous Catalysts", Abstracts of Papers Published in Neftekhimiya, vol. 28, No. 5, 684-694, 1988.
Chimi, "Beitrag zur katalytischen Cycloaminierung von Athanolaminen", vol. 22, No. 1, pp. 43-46, 1968.

* cited by examiner

*Primary Examiner* — Noble Jarrell
*Assistant Examiner* — John S Kenyon
(74) *Attorney, Agent, or Firm* — Kagan Binder, PLLC

(57) ABSTRACT

The invention provides a method for the reductive amination of diethanolamine to form a product composition that includes piperazine (PIP) and aminoethylethanolamine (AEEA). A catalyst with a transitional alumina/second metal oxide support and a mixture of catalytic metals is used for the reaction which results in low levels of non-PIP and non-AEEA side products.

13 Claims, No Drawings

REDUCTIVE AMINATION OF DIETHANOLAMINE AND RESULTING PRODUCT MIXTURE

CROSS REFERENCE TO RELATED APPLICATIONS

The present application claims priority to International Application No. PCT/US2012/064966, filed on Nov. 14, 2012, which in turn claims priority to and the benefit of U.S. Provisional Application No. 61/579,508, filed Dec. 22, 2011, the disclosure of which are hereby incorporated by reference in their entireties.

FIELD

The invention relates to the reductive amination of linear alkanolamines using a catalyst having an acidic mixed metal oxide support and catalytic metals thereon, and a product mixture formed therefrom.

BACKGROUND

Alkylamines, such as ethyleneamines, and alkanolamines, are known for their many uses in industry. Alkylamines can be broadly subcategorized into cyclic alkylamines and linear alkylamines. Piperazine (PIP) is a cyclic compound and the simplest cyclic member of the ethyleneamine family. Piperazine is used in the manufacture of plastics and resins (e.g., polyamides), other industrial materials, pesticidal compounds, and pharmaceutical compounds, such as anthelmintics With regards to alkanolamines, aminoethylethanolamine (AEEA) is an organic base with desirable chemical properties that make it a valuable intermediate for the synthesis of other compounds. The primary and secondary amine groups of AEEA, together with the hydroxyl group, combine the features of an ethyleneamine and an ethanolamine. AEEA has been used for the production of surfactants, fabric softeners, textile additives, fuel additives, chelates, and coatings.

Reductive amination of the linear alkanolamine diethanolamine (DEA) with ammonia is one way of producing PIP and AEEA. However the reductive amination of DEA can produce a variety, of non-PIP and non-AEEA products which can be of lesser economic value, and/or less useful for further processing by reductive amination. For example, U.S. Pat. No. 3,682,919 describes a process for preparing PIP and AEEA by subjecting DEA to reductive amination in the presence of a Ni—MgO (1:1) catalyst. DEA was reacted with ammonia and in the presence of the Ni—MgO catalyst at high temperatures 225° C. at a DEA conversion rate of 31 percent. Of the DEA reaction products a significant amount was non-PIP and non-AEEA products (9% monoethanolamine (MEA), 8% ethylenediamine (EDA), and 10% other amines, 27% total).

The inventors of the present application have found that these levels of non-PIP and non-AEEA products are undesirably high, and have accordingly discovered inventive methods for significantly improving the selectivity towards PIP and AEEA in the reductive amination of DEA with ammonia, while maintaining desirable reaction conditions, including moderate reaction temperatures and reactant quantities.

SUMMARY

The present disclosure generally provides methods useful for the reductive amination of diethanolamine (DEA) using a catalyst having an acidic mixed metal oxide support and catalytic portion including a mixture of catalytic metals immobilized on the support. Reductive amination of DEA using the catalyst compositions as described herein forms a desirable product composition that includes piperazine (PIP) and aminoethylethanolamine (AEEA).

The inventive methods provide a number of advantages. For example, the catalyst composition of the invention allows for the production, by reductive amination of DEA, of the desired PIP and AEEA products at high levels, while minimizing the formation of non-PIP and non-AEEA products. This improved selectivity in forming PIP and AEEA from DEA can be achieved at acceptable ammonia/DEA ratios (e.g., ~10:1) and temperatures, and modest DEA conversion rates. As such, conventional operating equipment (e.g., reactor equipment), operating conditions (e.g., time, temperature, and flow rate) and reactants (e.g., hydrogen gas and ammonia), can be used while still providing a substantially improved product mixture. Further, the use of temperatures that are lower than previously described processes of DEA reductive amination to PIP and AEEA (e.g., less than 200° C.) preserves the activity of the catalyst. Also, the AEEA produced in the reductive amination can be recycled and subjected to another cycle of reductive amination to generate additional PIP as a reaction product. Yet further, the method also allows a user to take advantage of the supply of DEA available in the amine industry.

Accordingly, one embodiment of the invention is a process for making a PIP- and AEEA-containing composition. The method comprises a step of providing a reaction composition comprising DEA. The method also comprises a step of subjecting the reaction composition to a reductive amination reaction in the presence of a catalyst composition ammonia. The catalyst composition comprises a support portion and a catalyst portion, with the support portion comprising an acidic mixed metal oxide comprising a transitional alumina and a second metal oxide, and the catalyst portion comprises a first metal selected from the group consisting of cobalt, nickel, and copper, and a second metal selected from the group consisting of rhenium, ruthenium, rhodium, platinum, palladium, and iridium. The reductive amination of DEA with ammonia forms products comprising PIP and AEEA in a product composition.

Another embodiment of the invention relates to product compositions formed by the method of the invention using the catalyst composition for the reductive amination of DEA with ammonia. In this embodiment, the product composition comprises PIP and AEEA, with PIP and AEEA together forming the majority of products in the composition, and wherein AEEA is present in an amount (wt %) that is greater than PIP.

DETAILED DESCRIPTION

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention. The invention is intended to cover all alternatives, modifications, and equivalents that may be included within the scope of the present invention as defined by the claims.

Throughout the specification and claims all percentages used herein are in weight percentages, unless otherwise indicated.

Generally, the invention is directed to methods for the reductive amination of diethanolamine (DEA) with ammonia in the presence of a catalyst composition to produce a product composition that includes piperazine (PIP) and aminoethylethanolamine (AEEA). The catalyst composition incorporates at least two different metals, one (a first) which is cobalt, nickel, or copper, and another (a second) which is a noble transition metal of the platinum group, such as ruthenium or rhenium. The first and second metals are immobilized on an acidic mixed metal oxide support. The acidic mixed metal oxide support comprises a transitional alumina (aluminum oxide ($Al_2O_3$)). These catalyst compositions can promote formation of PIP and AEEA as predominant products in the product composition, with low formation of undesired reaction products, as compared to catalysts that do not contain a transitional alumina-based acidic mixed metal oxide support as described. In the reductive amination, the catalysts provide high selectivity for desired PIP and AEEA products.

The reductive amination of DEA generates reaction products of PIP and AEEA as well as other non-PIP and non-AEEA reaction products such as monoethanolamine (MEA) and other amines as described herein, and these reaction products constitute a "product composition." Generally, the DEA conversion is not 100% and therefore unreacted DEA is mixed with the DEA reaction products in the output from the catalytic bed of the reactor. However, for purposes of illustrating the advantages of the invention with regards to formation of (DEA) reaction product, DEA is not defined as a part of the "product composition." Water is a byproduct of the reductive amination reaction. For purposes of simplicity, product compositions are reported on a dry, water-free basis.

The method of the invention provides a product composition with higher amounts of the desired PIP and AEEA reaction products, with lower quantities of non-PIP and non-AEEA reaction products. For example, the method of the invention is capable of providing non-PIP and non-AEEA reaction products at level of 15 wt % or less, and even 10 wt % of the reaction products in the product composition. The combined amount of PIP and AEEA can be provided at high amounts, such as about 75% wt or greater, about 80% wt or greater, about 85% wt or greater, and even 90% wt or greater of the products in the product composition.

Diethanolamine and ammonia are used as reactants to form the PIP- and AEEA-containing composition using the method of the invention. A DEA-containing composition can be obtained and used in the reductive amination method of the invention. Optionally, a method for preparing a DEA-containing composition can be performed prior to using the DEA-containing composition in the reductive amination method of the invention.

Various processes for preparing DEA are known in the art, and any one can optionally be performed prior to the reductive amination method of the present invention. Generally, diethanolamine is commercially prepared by the reacting ethylene oxide or ethylene halohydrins with ammonia. For example, ethylene oxide is generally allowed to react at temperatures of about 50° C. to 100° C. with an aqueous ammonia solution (15-50 wt. %). The reaction of ethylene oxide with aqueous ammonia (Reaction A) first produces monoethanolamine (MEA). MEA then reacts with a second and third equivalent of ethylene oxide to give DEA and triethanolamine (TEA), (Reaction B and C, respectively). The ratio of the MEA, DEA, and TEA products can be controlled by changing the stoichiometry of the reactants.

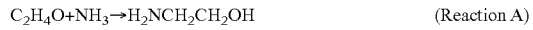  (Reaction A)

  (Reaction B)

  (Reaction C)

MEA, DEA, and TEA can be obtained by subjecting the reaction mixture to a series of separations. In some modes of practice separation of DEA from MEA and TEA can be carried out by chromatography. Commercially available analytical columns can be used to prepare a DEA composition. For example, Primesep™ 100 (SIELC Technologies, Prospect Heights, Ill.) is a reverse-phase analytical column with embedded acidic ion-pairing groups, which can separate ethanolamines such as MEA, DEA, and TEA by a combination of cation-exchange, hydrophobic, and polar interactions. The separation can use a mobile phase mixture of water, acetonitrile (MeCN, ACN) and trifluoroacetic acid (TFA).

Processes for the separation of DEA from MEA and TEA are also known in the art. For example, U.S. Pat. No. 3,849,262 describes providing a crude ethanolamine mixture to a distillation column, where MEA is withdrawn from the top of the column and DEA and TEA are withdrawn from the bottom of the column. A side stream consisting of MEA and ethylene glycol is taken from the column used for the distillation of the MEA and allowed to react with excess ethylene oxide, whereupon higher-boiling products, mainly DEA, are formed. Ethylene glycol can then be separated from DEA and TEA in the reaction product.

Another process for the separation of ethanolamines is described in U.S. Pat. No. 7,279,602 which describes distilling an ethanolamine mixture in two stages. The low-boiling fraction and the high-boiling fraction are taken off and discharged in the first stage and the intermediate-boiling fraction with TEA and DEA is distilled in the second stage.

A diethanolamine-containing reactant composition can be obtained, or optionally prepared, such as using a method of the prior art, and then used in the reductive amination method of the invention. DEA is a colorless liquid that has a molar mass of 105.14 g/mol, a melting point of 28° C. (82° F.), a boiling point of 217° C. (423° F.), and is water-soluble. Diethanolamine in the reactant composition can be provided in "neat" form as a liquid with no or no significant amount of solvent present. Alternatively, diethanolamine can be mixed with a non-reactive liquid such as water in the reactant composition. In some modes of practice, the reactant composition comprises diethanolamine and water, and diethanolamine is present as the primary component (i.e., greater than 50 wt. %), about 60 wt. % or greater, about 70 wt. % or greater, about 80 wt. % or greater, about 85 wt. % or greater, about 90 wt. % or greater, or about 95 wt. % or greater, in the composition.

The reactant composition with ammonia and DEA can be introduced into a reactor system that includes tubing, pump(s), valve(s), inlet port(s), heating element(s), a reactor bed with the catalyst composition, etc. In various modes of practice, the DEA-containing reactant composition is introduced into the reactor system and ammonia is introduced into the system into a flowing stream of DEA-containing reactant composition. In this case, ammonia mixes "in-line" with the DEA-containing reactant composition prior to entering the reactor bed with the catalyst composition. However, the invention also contemplates mixing (e.g., in bulk) the ammonia with DEA prior to introduction into the reactor system. As such, the DEA-containing reactant composition comprising ammonia can be provided to the reactor system, and in-line mixing is not required or optionally performed.

The DEA/ammonia containing composition is then used in a reductive amination reaction with a catalyst composition as descried herein to promote the formation of the PIP- and AEEA-containing composition. Features of the catalyst compositions will now be described in more detail.

The catalyst composition includes a support portion and a catalyst portion. A "support portion" refers to solid material that the metals of the catalyst portion are deposited on. The "catalyst portion" refers to the catalytic metals that are deposited on the support portion of the catalyst. The catalyst portion can be contiguous or non-contiguous on the metal portion. Other material or compounds may optionally be associated with the catalyst composition.

The support portion includes an acidic mixed metal oxide that comprises a transitional alumina and a second metal oxide. In some aspects of the invention, the transitional alumina comprises at least 50 weight percent of the support portion.

Transitional aluminas, or activated aluminas, are described in the *Encyclopedia of Chemical Technology, Volume 2, 5th Edition*, Kirk-Othmer (1992, page 221 et seq.) as a series of partially hydroxylated aluminum oxides (excluding alpha aluminas which are anhydrous in nature). In general, as a hydrous alumina precursor is heated, hydroxyl groups are driven off, leaving a porous solid structure. As the activation temperature increases through the transitional phases, the crystal structures become more ordered, thus allowing for identification of transitional aluminas by x-ray diffraction (hereafter "XRD"). The sequences of transition are affected not only by the starting materials, but also by the coarseness of crystallinity, heating rates, and impurities. The following transitions are generally accepted as the transitions when the starting material is coarse gibbsite in air:

gibbsite→boehmite→gamma→delta→theta→alpha alumina.

Of the transitional aluminas described above, the delta and theta phases can be particularly useful as a support portion of a catalyst composition in accordance with the methods of the invention. Other useful aluminas include mixtures of transitional aluminas and aluminas such as gamma/theta, gamma/delta, delta/theta, theta/alpha phases, or combinations thereof.

Transitional alumina carriers may be characterized using an X-ray diffractometer by methods known in the art. The following Table 1 lists the accepted 2-theta values for the aluminas, as supplied by the Joint Committee on Powder Diffraction Standards International Center for X-Ray Diffraction:

TABLE 1

| Aluminas | | | | | | | |
|---|---|---|---|---|---|---|---|
| gamma | 19.58 | 31.94 | 37.60 | 39.49 | 45.79 | 60.76 | 66.76 |
| delta | 17.65 | 19.49 | 21.82 | 31.14 | 32.78 | 34.74 | 36.96 | 39.49 |
| | 45.55 | 46.54 | 47.57 | 50.67 | 60.03 | 61.35 | 62.26 | 64.18 |
| | 66.76 | 67.31 | 73.33 | 75.37 | | | | |
| theta | 15.5 | 16.25 | 19.54 | 31.509 | 32.778 | 34.939 | 36.743 | 38.871 |
| | 39.911 | 44.856 | 46.4242 | 47.5849 | 50.6803 | 51.3931 | 52.6308 | 54.5575 |
| | 56.7218 | 58.7033 | 61.2553 | 62.3387 | 64.0501 | 65.3714 | 67.4008 | |
| alpha | 25.5 | 35.4 | 38.0 | 43.6 | 52.8 | 57.6 | 63.05 | 66.7 |
| | 68.4 | | | | | | | |

Catalyst supports of the invention may optionally include alumina employed in its hardest and most stable allotropic state, alpha-alumina (α-alumina) as a combination with a transitional alumina. In other catalyst supports of the invention, alumina can optionally be employed as gamma-alumina, in combination with a transitional alumina. Due to its small crystallite size, gamma-alumina is generally described as amorphous by XRD. However, in either of these cases, the transitional forms of alumina are desirably predominant in the alumina mixture.

As noted above, alpha alumina is not considered a transitional phase of alumina. Rather, alpha alumina is the most thermodynamically stable form of alumina at ambient conditions. Typically, then, alpha alumina is not present in a significant amount in the support portion of the inventive catalyst compositions. Although the crystallinity of alpha alumina is highly distinctive when compared to the transitional aluminas, in mixed phases that contain small amounts of alpha alumina, the amount of alpha alumina present is not easily quantified. However, due to the extremely low surface areas of alpha aluminas, useful mixed phases containing alpha alumina can be determined by those which fall within the surface area ranges described herein.

Similarly, while gamma alumina is not considered a transitional phase of alumina, it may also be present in the support portion. If optionally included, like alpha alumina, gamma alumina is desirably present only in a minor amount in the support portion. Useful mixed phases containing gamma alumina can be determined by those which fall within the surface area ranges described elsewhere herein.

Generally speaking, transitional aluminas are considered to be intermediate surface area supports. In accordance with the invention, support portions comprising transitional alumina can have surface areas in the range of about 10 $m^2$/g to about 200 $m^2$/g, or about 40 $m^2$/g to about 180 $m^2$/g, or about 80 $m^2$/g to about 180 $m^2$/g. Methods for measuring the surface area of a support are known in the art and include volumetric measuring methods, such as by measuring the volume of nitrogen gas adsorbed at various low-pressure levels by the catalyst sample. Pressure differentials caused by introducing the catalyst surface area to a fixed volume of nitrogen in the test apparatus are measured and used to calculate Brunauer-Emmett-Teller (BET) surface area.

As noted above, transitional aluminas can be obtained by heat-treating transitional alumina precursor materials such as gibbsite, boehmite, or bayerite to the desired phase transformation temperature. Processing can involve heat treatment of a transitional alumina precursor into transitional alumina, in the form of delta or theta alumina, or combinations thereof. Other techniques rely upon direct synthesis via a wet chemical processing, such as through hydrolysis of aluminum alkoxide.

Another way of forming transitional alumina material is through a seeded processing pathway, such as that described in PCT/US2005/042048 ("Transitional Alumina Particulate Materials Having Controlled Morphology and Processing for Forming Same," Bauer et al.) and U.S. Patent Publication No. 2008/0003131 A1 ("Transitional Alumina Particulate Materials Having Controlled Morphology and Processing for Forming Same," Bauer et al.). The transitional alumina can be present as a mass of particulate material, composed of particles that may be fully dispersed, partially agglomerated, or fully agglomerate. In the dry form, the particulate material may be in the form of a powder. This process typically includes providing a boehmite precursor and boehmite seeds in a suspension, sol or slurry. The suspension, sol or slurry can be heated treated (such as by hydrothermal treatment) to convert the boehmite precursor into boehmite particulate material formed of particles or crystallites. Heat treatment is then carried out to the boehmite particulate material to effect polymorphic transformation into transitional alumina.

The transitional alumina precursor can be heat treated by calcination at a temperature sufficient to cause transformation into a transitional phase alumina, or a combination of transitional phases. Typically, calcination or heat treatment can be carried out at a temperature greater than about 250° C., but lower than about 1100° C. At temperatures less than 250° C., transformation into the lowest temperature form of transitional alumina, gamma alumina, typically will not take place. At temperatures greater than 1100° C., typically the precursor will transform into the alpha phase. Calcination can be carried out at a temperature greater than 400° C., such as not less than about 450° C. The maximum calcination temperature may be less than about 1050° C. or 1100° C., these upper temperatures usually resulting in a substantial proportion of theta phase alumina, the highest temperature form of transitional alumina.

When it is desired to form a substantial content of delta alumina, the transitional alumina precursor can be calcined at a temperature lower than about 950° C., such as within a range of about 750° C. to about 950° C. Alternatively, calcination can be performed at temperatures above about 750° C., or above about 775° C., or above about 800° C., to avoid transformation into a predominant gamma phase alumina.

Calcination of the transitional alumina precursor can be carried out in various environments including controlled gas and pressure environments. Because calcination is generally carried out to effect phase changes in the precursor material and not chemical reaction, and since the resulting material is predominantly an oxide, specialized gaseous and pressure environments need not be implemented in most cases.

Typically, calcination can be carried out for a controlled time period to effect repeatable and reliable transformation from batch to batch. Calcination times typically range from about 0.5 minutes to about 60 minutes, typically about 1 minute to about 15 minutes.

Generally, as a result of calcination, the alumina material used to form the support portion is predominantly (more than 50 weight percent) transitional alumina. The precise makeup of transitional alumina phases may vary according to the support portion desired, such as a blend of transitional phases. A predominant amount of a particular transitional phase can be present, such as at least about 50 weight percent, or at least about 60 weight percent, or at least about 70 weight percent, or at least about 80 weight percent, of a desired transitional phase. The transitional alumina can comprise essentially a single phase of transitional alumina (e.g., at least 95 weight percent, or at least about 98 weight percent, or even up to about 100 weight percent of a single phase of transitional alumina). As discussed herein, the particular phase(s) of transitional alumina can be determined by XRD.

Illustrative aluminas suitable for inclusion in the support portion include delta, theta, gamma/delta, gamma/theta, delta/theta, and theta/alpha phases. If alpha alumina is included in the alumina support portion, it can be present in an amount that is about 49 weight percent or less. If gamma alumina is included in the alumina support portion, it can be present in an amount that is about 49 weight percent or less. The support can include one or more of the following additional alumina transitional phases: kappa, eta, rho, and chi, and combinations thereof.

In the support portion, the alumina is combined with a second metal oxide to provide an acidic mixed metal oxide. Illustrative second metal oxides include oxides that, when combined with the alumina, can provide sufficient surface acidity. Some binary metal oxides are known to have surface acidity and have been used as solid acid catalysts, such as silica-alumina and alumina-boron oxide. Additional mixed metal oxides that may generate surface acidity can be determined using the hypothesis described by Tanabe et al. (*A New Hypothesis Regarding the Surface Acidity of Binary Metal Oxides*, Bulletin of the Chemical Society of Japan, 47(5): 1064-1066 (1974)).

Exemplary second metal oxides comprise at least one element selected from Group IIA, IIIA, IVA, VA, VIA, IIB, MB, IVB, VB, VIB, VIIB and a rare earth element of the Periodic Table. Illustrative second metal oxides in accordance with include silicon, lanthanum, magnesium, zirconium, boron, titanium, niobium, tungsten and cerium. In some embodiments, the second metal oxide can comprise silicon.

Acidic mixed metal oxides can be prepared by one skilled in the art. Such known preparation methods include coprecipitation of metal salts, sol-gel techniques, ion exchange, mechanical mixing, and incipient wetness or precipitation on metal oxides.

The acidic mixed metal oxide support portion can be provided in any convenient morphology. The shape of the support will typically depend upon the shape required by the particular apparatus used to perform the reductive amination reaction. Catalyst compositions can be made on supports in the form of particles, powders, spheres, extrudates, pellets (cut extrudates), trilobes, quadrilobes, rings, monoliths, and pentarings. Particles can have an elongated morphology, which can be described generally in terms of the particle's aspect ratio. The aspect ratio is the ratio of the longest dimension to the next longest dimension perpendicular to the longest dimension. Alternatively, particles can have a platelet-shape, wherein the particles generally have opposite major surfaces, the opposite major surfaces being generally planar and generally parallel to each other.

Morphology of the support portion can be further described in terms of support portion size, more particularly, average support portion size. Average support portion size can be described as the average longest or length dimension of the support material. Average support portion size can be determined by taking multiple representative samples and physically measuring the support material sizes found in representative samples. Such samples may be taken by various characterization techniques, such as by scanning electron microscopy (SEM). For example, the support portion can be provided in the form of an extrudate. Extrudates ranging in diameter of about ⅛" (3.175 mm) or less can be useful, for example in the range of about 1/32" (0.79375 mm) to about ⅛". Another useful form of the support portion is a trilobe. Trilobes having a diameter of about ⅛" or less can be useful, for example in the range of about 1/16" (1.5875 mm) to about ⅛". Yet another useful support form is a sphere, such as spheres having a diameter of 3 mm or less.

In addition to the shape and average support material size, yet another useful way to characterize morphology of the support portion is to describe the specific surface area of the support portion. The acidic metal oxide complex can be provided with a range of surface areas ($m^2/g$), as measured by the commonly available BET technique. The support portion can have a relatively high specific surface area, such as not less than about 10 $m^2/g$, not less than about 40 $m^2/g$, or not less than about 80 $m^2/g$, or not less than about 90 $m^2/g$. Since specific surface area is a function of particle morphology as well as size, the specific surface can also be less than about 200 m$^2$/g, such as less than about 150 m$^2$/g, or less than about 100 m$^2$/g. For example, the surface area can be in the range of about 80 m$^2$/g to about 180 m$^2$/g.

Other useful characteristics of the support portion may include pore volume (expressed as Hg intrusion values or N$_2$ values), and water absorption (expressed as a percentage of the dry sample weight). Illustrative pore volume (Hg pore symmetry) ranges are about 0.3 cm$^3$/g to about 1 cm$^3$/g. Another characteristic of the support may be the median pore diameter. Additionally, the support may have a pore size distribution that is unimodal or multimodal (e.g., bimodal, trimodal, etc.).

The catalyst compositions used for the reductive amination method have a catalyst portion that comprises a combination of metals. The combination of metals in the catalyst portion includes a first metal selected from cobalt, nickel, and copper, and a second metal selected from the group consisting of rhenium, ruthenium, rhodium, platinum, palladium, and iridium (i.e., the "platinum group").

As used herein, the total amount of the catalytic metals in the compositions is referred to herein as the "catalyst portion," and the amount of the catalyst portion can be expressed as a percentage by weight of the catalytic composition. The catalyst portion can be prepared with a total amount of metals of 25 wt. % or less of the total weight of the catalyst composition. Lower amounts of the catalyst portion can be used, such as about 20 wt. % or less, for example in the range of about 6 wt. % to about 16 wt. %, or more specifically about 8 wt. % to about 14 wt. % of the total weight of the catalyst composition. A catalyst composition that is 10 wt. % of the catalyst composition has 10 g of catalyst metals associated with 90 g of the support. Generally, the catalyst portion includes a sufficient amount of metals to provide the desired catalytic activity in the reductive amination of DEA to PIP and AEEA. The lower loading of the catalytic metals on the support can provide an economic advantage while still providing desirable catalytic activity and selectivity.

Exemplary catalyst compositions include a catalyst portion with a first metal selected from cobalt, nickel, and copper in an amount of less than 20 wt. %, or about 15 wt. % or less, such as in the range of about 4 wt. % to about 12 wt. %, or in the range of about 6 wt. % to about 10 wt. % of the catalyst composition. In one exemplary catalyst composition, nickel is present in an amount of about 8.0 wt %.

Exemplary catalyst compositions include a catalyst portion with a second metal selected from rhenium, ruthenium, rhodium, platinum, palladium, and iridium in an amount of less than 5 wt. %, or about 4 wt. % or less, such as in the range of about 0.5 wt. % to about 4 wt. %, or in the range of about 1 wt. % to about 2 wt. % of the catalyst composition. In one exemplary catalyst composition, rhenium is present in an amount of about 2.0 wt %.

The amount of the first and second metals of the catalyst portion can also be expressed as predetermined weight ratio. In some cases, the weight ratio of the first and second metals in the catalyst portion is in the range of about 10:1 to 1:1, respectively. In more specific cases, the weight ratio of the first and second metals in the catalyst portion is in the range of about 8:1 to 2:1. In one exemplary catalyst composition, first and second metals are present in a weight ratio of about 4:1.

The catalyst portion can optionally include boron. If present, boron can be used in small amounts, such as less than the second metal of the catalyst portion. For example, boron can be present in an amount of less than 2.5 wt. %, or about 2 wt. % or less, such as in the range of about 0.1 wt. % to about 2 wt. %. In some modes of practice the catalyst composition is prepared without including boron.

In one exemplary catalyst composition, nickel is present in an amount of about 8.0 wt %, rhenium is present in an amount of about 2.0 wt %, and boron is present in an amount of 1.6 wt. %.

Various methods can be carried out for depositing the mixture of metals on the catalyst support to provide the catalyst portion. In some modes of practice, the one or more metals of the catalyst portion are associated with the support portion by impregnation. Impregnation is particularly suitable for this process, since lower metal loadings are used.

Although impregnation is one mode of preparing the catalytic support, other methods can be used to deposit the catalytic metals on the support portion. For example, the metals can be deposited on the support material by co-precipitation, sol-gel techniques, chemical vapor deposition, or ion exchange. In order to describe the process of depositing the catalytic metal(s) with the support, steps of an impregnation method will be described.

In some modes of practice the metals of the catalytic portion are deposited on the support using an incipient wetness technique, often referred to as incipient wetness impregnation (IW or IWI). In this technique an active metal precursor (or combination of active metal precursors) is dissolved in an aqueous or organic solution. The metal-containing solution ("impregnation solution") is added to a catalyst support. Often, the impregnation solution is added in a volume that is the same as the pore volume of the support. Capillary action draws the impregnation solution into the pores of the support. The impregnated support can then be dried and calcined to drive off the volatile liquids of the impregnation solution. This process deposits the catalytic metal or metals on the surface of the support portion.

In some modes of practice, an aqueous solution of a salt of the metal is prepared (the impregnation solution). More than one metal can be immobilized using an impregnation solution having a mixture of salts of the desired metals. The impregnation solution can be saturated with the one or more metal salts, or the one or more metal salts can be used in amounts less than saturation. The concentration of the one or more metal salts in the impregnation solution can depend on factors such as the desired amount of metal(s) to be deposited on the support, and the solubility of the particular metal salt(s) used in the process.

Inorganic and/or organic salts can be used to prepare the impregnation solution.

Organic and inorganic salts of nickel include, but are not limited to, nickel nitrate hexahydrate, nickel formate, nickel acetate tetrahydrate, nickel acetate, nickel chloride, nickel carbonate and the like. A nickel-containing impregnation solution can be prepared containing one or more of these nickel salts. In some modes of practice, nickel nitrate or nickel formate is used to prepare the impregnation solution.

Precursor salts of rhenium include potassium and ammonium salts. Additionally, perrhenic acid may also be used. A rhenium-containing impregnation solution can be prepared containing one or both of these salts.

Organic and inorganic salts of cobalt include, but are not limited to, cobalt bromide, cobalt carbonate, cobalt chloride, cobalt fluoride, cobalt hydroxide, cobalt nitrate, cobalt nitrate hexahydrate, cobalt oxalate, cobalt perchlorate, cobalt phosphate, and cobalt sulfate.

Organic and inorganic salts of copper include, but are not limited to, copper gluconate, copper formate, copper chloride, copper bromide, copper fluoride, copper hydroxide, copper nitrate hydrate, copper sulfate pentahydrate, and copper pyrophosphate hydrate.

In many modes of practice, the one or more metals to be deposited on the support are dissolved in a suitable solvent, such as deionized water, for preparation of the impregnation solution. In one mode of practice, precursor salts of nickel and rhenium are dissolved in 70-80° C. water to form an impregnation solution.

One or more impregnation solutions can be prepared to provide the type(s) and total amount of metal(s) to be deposited on the support portion. Since a lower amount of metal is associated with the support, the total amount of metal can be deposited in a limited number of applications. For example, the total amount of metal deposited can be applied in one, two, three, or four applications. Although an impregnation solution can be prepared with a high concentration of metal salt (i.e., a minimal amount of water), in some cases the total amount of the impregnation solution to be applied may be more than what the alumina support can hold by absorption. Therefore, in some modes of practice, the impregnation solution is applied to the support in multiple steps, wherein a portion of the impregnation solution about equal to the absorption volume of the support is applied to the support in one application step. Incorporation of additional metal(s) into the support may be further increased by techniques known to those skilled in the art, such as increasing the time the support is in contact with the solution.

The impregnation solution can be applied to the support using various methods. For example, the solution can be applied processes such as drip application, by immersion (e.g., dipping), or by spraying. During application, the support can be agitated by processes such as mixing, tumbling, stirring, or shaking. Mechanical equipment can be used to facilitate agitation. Agitation during the application of the impregnation solution can increase the uniformity of the impregnation solution applied to the support.

After all or a portion of the impregnation solution is applied to the support, the support can be dried. In the drying step, the liquid which solvates the metal salt is volatized and removed from the support. The drying may be accomplished by any technique that sufficiently evaporates the volatile constituents of the impregnation solution. The drying step can comprise a calcination step, as further discussed herein. Multiple drying steps can be performed if the impregnation solution is applied in more than one step. Therefore, an overall process for preparing the catalyst composition can include multiple steps of disposing the application composition, and then drying the impregnated support. The steps of depositing and then drying can be performed until all of the impregnation solution is used.

Typically, the impregnated support is dried at a temperature of above 100° C. The elevated temperature can also be accompanied by a reduced pressure environment to accelerate removal of the liquid from the support. The support can be dried in air or in the presence of an inert gas, such as nitrogen. Drying is carried out for a period of time sufficient for removal of most or all of the liquid of the impregnation solution. In some modes of practice, the step of drying is performed for a period of about one hour or more at elevated temperatures.

The process of preparing the catalytic composition can also involve one or more steps of calcining the support. One or more steps of calcining the support can be performed in the absence of the catalytic metals, and optionally in the presence of the catalytic metals, or both.

In some modes of practice, given the high heat of calcination, drying and removal of the liquid component of the impregnation solution occurs. Therefore, as used herein, calcination of the support meets the requirements of the drying step or steps, which are typically performed following application of the impregnation solution. In addition, calcination can cause conversion of the metal salts into oxides. The choice of a particular calcination temperature can depend on the decomposition temperature of the salts used.

Calcination normally takes place at temperatures below the melting point of the materials used to form the support portion of the catalytic composition. For example, calcination is typically performed in the range of about 200° C. to about 1200° C., and more typically in the range of about 300° C. to about 500° C. Calcination can take place for minutes to hours (e.g., two or three or more hours). Calcination can be carried out in the presence of air, or under inert gas. In one mode of practice, cobalt and ruthenium salts are deposited on the support portion. The impregnated support is then calcined at a temperature of about 340° C.

In some modes of practice calcination is performed after one or more steps of applying the impregnation solution. After all of the impregnation solution has been applied the metal-loaded support can be calcined for a longer period of time to ensure substantial removal of the impregnation solution liquid. For example, in some specific modes of practice, the impregnation solution is applied to the support in two or more steps, with calcination at about 340° C. for about one hour in air performed after each step of applying, with a final calcination at about 340° C. for about one hour in air.

Following metal impregnation and calcination, the catalyst composition can be reduced, converting the metal oxides produced in the calcination step to the reduced metal form. Typically, the metal-containing support is reduced in the presence of hydrogen. The metal-containing support can be contacted with hydrogen gas at a temperature that is about in the same range as that used for calcination. The process of reduction can be carried out from about 30 minutes to about 24 hours, or more.

Following reduction, the catalyst composition can be stabilized with gentle oxidation. Typical stabilizing treatments involve contacting the reduced catalyst composition with oxygen or carbon dioxide. For example, in one mode of practice, the catalyst composition is treated with about 1% $O_2/N_2$. Prior to using in an animation reaction, the catalyst composition must be activated with hydrogen.

After impregnation and drying/calcination (with optional reduction) the catalyst composition can optionally be stored or handled in an inert environment.

Optionally, the catalyst portion can be deposited on a porous support portion so that at least the active catalyst metals are provided in a very thin outer layer or "egg shell" structure. This catalyst structure can also lower the active metal requirement for the catalyst composition, and/or maximize contact of the active metals with the amine-containing elements within the reaction solution. Methods described in U.S. Pat. No. 5,851,948 can be utilized to create a similar "egg shell" structure for the present inventive catalyst compositions. For example, the catalytic metals comprising the catalyst portion (here, nickel and ruthenium) can be added to the support portion as a thin outer layer or shell on the support portion. This technique of depositing an active metal such as nickel and/or ruthenium in a thin layer or shell on only the outer surface of the support portion advantageously provides a high localized concentration of the active metals on the catalyst outer surface, where it is readily contacted by the amine-containing, compounds in the reaction solution. Techniques described in U.S. Pat. No. 5,851,948 (Chuang et al., "Supported Catalyst and Process for Catalytic Oxidation of Volatile Organic Compounds") can be instructive in accordance with these supports.

Exemplary catalyst composition diameters can be in the range of about 0.8 mm to about 3.1 mm; surface area can be in the range of about 10 m$^2$/g to about 200 m$^2$/g; catalytically active metal concentration can be in the range of about 1 weight percent to about 25 weight percent, and the catalyst portion can be provided as a thin outer shell on the support portion.

Catalytic metal can also be deposited on the surface of the support portion according to techniques described by Komiyama et al. ("Concentration Profiles in Impregnation of Porous Catalysts: Nickel on Alumina," J. of Catalysis 63, 35-52 (1980)). Utilizing the principles described by Komiyama et al., radial concentration profiles in the catalyst compositions can be formed by impregnating the support portion with aqueous catalytic metal (e.g., nickel and ruthenium) solutions.

In still further embodiments, internal mass transfer resistance can be controlled by selecting a desirable particle size for the support portion. As discussed in European Patent Application No. EP 1249440 A1 ("Process for Preparing Linear Alkylbenzenes," Wang et al), both the catalyst particle size and porosity can be adjusted to provide a desired conversion and catalytic stability.

In use, the catalyst composition is used to promote the reductive amination of DEA in a reactant composition to PIP and AEEA. The amount of catalyst composition that is used can be determined based on one or more of the following factors: the type and amount of reactants, the reactor (reaction vessel) configuration, the reaction conditions (such as temperature, time, flow rate, and pressure), the degree of conversion to a desired product(s), and the selectivity desired (i.e., the ratio of the desired product over an undesired product). The catalyst composition is present in the reaction zone in a reaction system in sufficient catalytic amount to enable the desired reaction to occur.

The general reaction for the process is shown below:

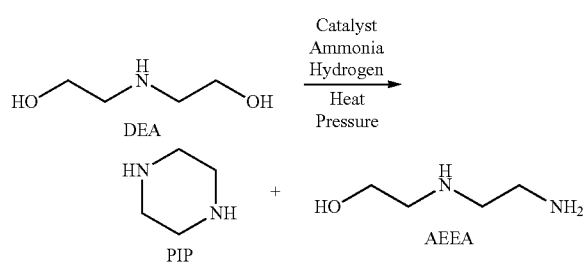

The reactants for reductive amination reaction include DEA and ammonia, which are mixed to form a reactant composition. Reductive amination of DEA using ammonia is performed in the presence of the catalyst composition and hydrogen, with elevated temperature and pressure. The compounds found in the product composition (i.e., the output of the reaction) include reductively aminated products, with PIP and AEEA representing the two predominant compounds by weight percent in the product composition. For example, in a composition with products A, B, C, D, E, F, and G, wherein by weight percent, A>B>C>D>E>F>>G, A and B are the two predominant products. Other "secondary" compounds may be found in the product composition, including monoethanolamine (MEA), diethylenetriamine (DETA), aminoethylpiperazine (AEP), hydroxyethylpiperazine (HEP) and linear tetraethylenepentamine (L-TEPA). However, because of the high selectivity of the reductive amination using the catalyst to form PIP and AEEA, the amount of secondary compounds (taken collectively) present in the product composition is less than either the amount of PIP or AEEA. While DEA and ammonia can flow out of the reactor bed as an unreacted starting material, they are not considered part of the product composition for purposes of discussion of the invention. Likewise, water is a byproduct of reductive amination, but is not considered part of the product composition for purposes of discussion of the invention.

Operating conditions can be chosen to provide a desired rate of conversion, which has been shown to affect the selectivity for the desired products PIP and AEEA. In particular, conditions are established to provide a certain rate of conversion of DEA, resulting in a desired selectivity for PIP and AEEA. For purposes of this invention, "DEA conversion" refers to the total weight percentage of DEA consumed as a result of conversion. The conversion can vary depending upon factors such as the reactants, catalyst, process conditions, and the like. In many embodiments, the conversion (e.g., of DEA) is at least about 10%, and desirably less than about 50%, and in some modes of practice in the range of about 20% to about 40%, or more specifically about 25% to about 35%. In some modes of practice the desired conversion of DEA is about 31%.

The temperature of reaction can be selected to provide a desired degree of conversion, which is discussed herein. Generally, reaction temperatures for the reductive amination method falls within the range of about 140° C. to about 190° C., and in desired modes of practice a reaction temperature in the range of about 150° C. to about 180° C. is used. The temperature may be varied or may vary throughout the reaction process, and may fluctuate up to about 30%, or up to about 20% of the starting temperature. In many modes of practice, the temperature is chosen to provide a relatively low rate of conversion of DEA (e.g., less then 40%).

For purposes of the invention, "selectivity" refers to the dry weight percentage of converted reactant(s) that form the desired aminated products PIP and AEEA. In some modes of practice the percent selectivity to PIP is about the range of about 15% to about 25%. In some modes of practice the percent selectivity to AEEA is in the range of about 70% to about 80%. Like conversion, selectivity will vary based upon factors including the conversion of the reactant(s), feed reactants, catalyst, process conditions, and the like. In view of the current disclosure and examples illustrative of the invention, the skilled artisan will appreciate that selectivity can be affected in the present system by adjusting reaction temperatures or residence time.

Along with the catalyst composition as described herein, reductive amination can be performed using any suitable method and reaction equipment. For example, reductive amination can be carried out using a continuous process, a semi-continuous process, a batch-wise process, or a combination of these processes. In one desired mode of practice a continuous process in a conventional high-pressure equipment with a heating feature. The equipment can have one or more features which cause movement of the reactants and/or catalysts in the equipment, such as an agitator or pump. Various reactor designs can be used, such as a stirred-tank, fixed-bed, slurry, or fluid-bed reactors. The reactors can be designed for liquid-phase, gas-phase, multi-phase or super-critical conditions.

In some modes of practice, the DEA reactant is provided to the reaction bed that includes the catalyst composition as a stream, the stream having continuous flow. The reactant feed can be upflowing or downflowing. Design features in the reactor that optimize plug flow can also be used. Effluent from the reaction zone is also a stream comprising the unreacted components of the feed stream (DEA) and the reaction products including PIP and AEEA. In some modes of practice, a liquid DEA is established in an upflow direction into the catalyst bed. In some modes of practice, a flow rate is established to provide a space velocity in the range of about 4 gmol/hr/kg catalyst to about 8 gmol/hr/kg catalyst, with an exemplary space velocity of about 5.8 gmol/hr/kg catalyst.

The reductive amination reaction of DEA is carried out in the presence of a nitrogen-providing reactant, with ammonia commonly being used as the reactant. Ammonia can be included prior to and/or within the catalyst bed in an amount sufficient to provide a desired rate of conversion and desired product selectivity. For example, ammonia can be fed into the DEA stream prior to the DEA entering the catalyst bed. The amount of ammonia introduced can, in some cases, be defined as the ratio between the ammonia and the reactant DEA. Ammonia:DEA ratios are in the range of about 5:1 to 50:1, with an exemplary ratio of about 9.4:1.

The reductive amination reaction can be carried out in the presence of hydrogen or nitrogen gas. Hydrogen may facilitate the production of the reaction product, and inhibit or reduce poisoning of the catalyst and can be included prior to and/or within the catalyst bed in an amount sufficient to affect catalyst activity and product selectivity. For example, hydrogen gas can be fed into the DEA stream prior to the DEA entering the catalyst bed. Hydrogen concentration can be in the range of 0.001 to 10.0 mole % based on liquid feed, with an exemplary hydrogen concentration of 1.1 mole %.

Typical reaction pressures range from about 200 psig to about 5000 psig, about 1500 psig to about 3500 psig, or more specifically about 1800 psig to about 3000 psig The reductive amination of DEA using the catalyst described herein provides a "product composition" that includes a mixture of DEA reaction products including PIP and AEEA. Since DEA and ammonia are not reaction products, for purposes of explaining aspects of the "product composition" the amount of DEA and ammonia are not considered unless otherwise noted. The product composition can be described in various ways, such as by the percent dry weight of one or more of the DEA reaction products in the product composition, or the weight ratio of one or more DEA reaction products to one or more other DEA reaction products in the dry product composition.

For example, in some preparations, the combined amount of PIP and AEEA represents about 75% wt or greater of the products in the product composition, about 80% wt or greater of the products in the product composition, about 85% wt or greater of the products in the product composition, or about 90% wt or greater of the products in the product composition. In one exemplary preparation the combined amount of PIP and AEEA represent about 93% wt or greater of the products in the product composition.

In some preparations, PIP is present in an amount of less than or equal to about 40% wt, less than or equal to about 30% wt in the product composition, such as in the range of about 15% wt to about 30% wt or about 15% wt to about 25% wt.

In some preparations, AEEA is present in an amount of about 40% wt or greater in the product composition, about 50% wt or greater in the product composition, about 60% wt or greater in the product composition, or about 70% wt or greater in the product composition, such as in the range of about 40% wt to about 80% wt or about 40% wt to about 60% wt.

In some preparations, the total amount of non-PIP and non-AEEA products present in the product composition is preferably less than or equal to about 15% wt or less, or less than or equal to about 10% wt or less of products in the product composition. In one exemplary preparation the total amount of non-PIP and non-AEEA products present in the product composition is about 7% wt. However, in some preparations, amounts of non-PIP and non-AEEA products that are less than or equal to about 25% wt, or less than or equal to about 20% wt, may be allowed in the product composition.

The products in the product composition can be subjected to one or more separation step(s). For example, hydrogen and ammonia (the low molecular weight compounds) can be separated from unreacted DEA and the reductive amination products of DEA by fractional distillation. Piperazine can also be separated from the DEA and non-PIP reductive amination products by fractional distillation.

In some modes of practice, unreacted DEA and optionally AEEA, are returned to the reaction system following removal of PIP and, optionally, non-PIP and non-AEEA products from the product composition. For example, following fractional distillation a second reaction composition including DEA and AEEA are recycled back into the reactor system and are subjected to another reductive amination step using the catalyst composition to generate piperazine.

Commercial piperazine is often sold in aqueous solutions to facilitate handling and storage due to its narrow liquid range, having a relatively high freezing point of 110° C. (230° F.) and a boiling point of 146° C. (295° F.) at 760 mm Hg.

The invention will now be described with reference to the following non-limiting Examples.

EXAMPLES

The following Examples illustrate aspects of the invention.

Unless otherwise noted, catalyst compositions were prepared using the following generalized procedure. Precursor salts of the metals (nickel and rhenium) were dissolved in 70-80° C. water to form an impregnation solution. The final volume of the impregnation solution was adjusted to equal the adsorption volume required for the number of times that the support was impregnated, and the quantities of the precursor salts were those calculated to give the metal compositions provided in the Examples. In each case the support was impregnated to incipient wetness by the addition of the appropriate amount of impregnation solution and gently agitated until all the liquid was adsorbed. The sample was then placed in a muffle furnace and calcined in air for one hour at 340° C. or as otherwise specified in the Examples. When the support had cooled, additional impregnations were performed until all of the solution had been added. A calcination step at 340° C. was done after each impregnation.

Those skilled in the art will readily appreciate that impregnation with the impregnation solution can optionally be performed in one, two, four or more incipient wetness applications, as dictated by such variables as the solubility of the precursor sales, the porosity of the support to be impregnated, and the desired weight loading of the metal.

Prior to use, the catalyst compositions were reduced in hydrogen at 340° C. The catalyst compositions were then passivated with a dilute oxygen stream to facilitate handling in the open atmosphere. The catalyst composition for the reductive amination diethanolamine, as described below.

Example 1

Reductive amination of DEA was run in a 1 inch by 8 foot seamless Swagelok™ tubing packed bed reactor with 400 grams of a catalyst composition having a nominal catalyst portion of 8.0 wt. % nickel, 2.1 wt. % rhenium, and 1.6 wt. % boron on alumina-silica (70:30) support portion. DEA was fed using an Isco™ syringe pump. DEA was pumped through a flow meter, a preheater, and combined with ammonia and hydrogen before entering the bottom of the reactor. The reactor bed is encased in 1.5 inch diameter Swagelok™ tubing through which heat transfer fluid is pumped via a standard laboratory heating bath. This allowed for virtually isothermal operation of the reactor tube. A multipoint thermocouple was placed inside the reactor bed for temperature monitoring. Temperature and pressure was monitored at various points in the reactor system.

The DEA space velocity (SV) was held constant at 5.8 gmol/hr/kgcat. The $H_2$ concentration was held constant at 1.1 mole percent. The ammonia/DEA mole ratio was 9.4. Gas chromatography analysis of the products from the reductive amination is shown in Table 2.

TABLE 2

| | Product GC Analysis (ISTD Concentration)* | | | | | | | | |
|---|---|---|---|---|---|---|---|---|---|
| Rx Avg. Temp (° C.) | MEA (wt %) | PIP (wt %) | DETA (wt %) | AEEA (wt %) | AEP (wt %) | DEA (wt %) | HEP (wt %) | L-TEPA (wt %) | DEA Conversion (%) |
| 148 | 1.02 | 1.54 | 0.21 | 12.00 | 0.00 | 85.10 | 0.00 | 0.13 | 17.6% |
| 152 | 0.48 | 2.21 | 0.36 | 14.69 | 0.00 | 82.16 | 0.00 | 0.12 | 23.8% |
| 156 | 0.52 | 3.03 | 0.54 | 16.51 | 0.09 | 79.19 | 0.00 | 0.11 | 25.9% |
| 157 | 0.60 | 3.85 | 0.68 | 18.99 | 0.00 | 75.71 | 0.10 | 0.07 | 28.5% |
| 160 | 0.78 | 5.55 | 1.01 | 21.41 | 0.00 | 71.08 | 0.08 | 0.10 | 31.0% |
| 163 | 0.90 | 8.33 | 1.29 | 24.33 | 0.00 | 64.83 | 0.25 | 0.08 | 37.8% |

*The GC results are on a water-free basis.

Example 2

Another reductive amination of DEA was performed in a reactor system having a down-flow tubular reactor fabricated of nominal 1" outside diameter 316 SS that was 92" in length. The reactor inside diameter was 0.688". The reactor was charged with 125-250 g of a catalyst composition with a nominal catalyst portion of 8.0 wt. % nickel, 2.1 wt. % rhenium, and 1.6 wt. % boron on an alumina-silica (80:20) support portion. An inlet zone (of varying length) was filled with glass shot to act as a preheater for the feed. The reactor was provided with several thermocouple ports to allow for monitoring catalyst bed temperatures. The reactor feed consisted of DEA/$H_2O$ (80:20 wt. %), to which was added hydrogen gas and liquid ammonia. Mixing was achieved in a feed heater prior to the reactor.

The DEA SV ranged from 6.1 to 9.7 gmol/hr/kgcat. The $H_2$ concentration was held relatively constant from 1.5 to 1.7 mole percent. The ammonia/DEA mole ratio ranged from 27 to 47. Gas chromatography analysis of the products from the reductive amination is shown in Table 3.

TABLE 3

| Rx Avg. Temp (° C.) | Product GC Analysis (ISTD Concentration)* | | | | | | | DEA Conversion (%) |
|---|---|---|---|---|---|---|---|---|
| | MEA (wt %) | PIP (wt %) | DETA (wt %) | AEEA (wt %) | AEP (wt %) | DEA (wt %) | Others (wt %) | |
| 169 | 1.51 | 1.18 | 0.24 | 8.01 | 0.22 | 88.19 | 0.63 | 12.03 |
| 169 | 0.69 | 1.20 | 0.24 | 8.26 | 0.19 | 88.99 | 0.44 | 11.37 |
| 174 | 0.61 | 1.83 | 0.40 | 10.48 | 0.25 | 85.82 | 0.61 | 14.73 |
| 174 | 0.63 | 1.74 | 0.37 | 10.08 | 0.23 | 86.33 | 0.62 | 14.19 |
| 179 | 0.82 | 3.84 | 0.93 | 15.43 | 0.39 | 77.24 | 1.36 | 23.77 |
| 179 | 0.66 | 2.85 | 0.67 | 13.20 | 0.34 | 81.28 | 1.02 | 19.53 |

*The GC results are on a water-free basis.

Example 3

Comparative

Table 4 includes results as described in example 8 of In U.S. Pat. No. 3,682,919. In this example, the results were obtained from a 300 mL autoclave with a Ni—MgO catalyst which was obtained by evaporation of an equimolar solution of nickel and magnesium formate, followed by thermal decomposition of the mixed salt at 330° C. A total of 30.9 grams of DEA and 50 grams of anhydrous ammonia and 3.24 grams of the catalyst was charged to the reactor and heated to 225° C. for three hours. The ammonia/DEA mole ratio was 10:1. The products of the '919 patent are compared to those obtained in Example 1. Product analysis is on a water and DEA free basis.

TABLE 4

| | Product GC Analysis (DEA and H2O free) | | | | |
|---|---|---|---|---|---|
| Examples | MEA (wt %) | PIP (wt %) | AEEA (wt %) | Other (wt %) | DEA Conversion (wt %) |
| '919 patent | 9 | 47 | 26 | 18 | 31 |
| Example 1 | 2.7 | 19.2 | 74.0 | 4.1 | 31 |

As compared to the U.S. Pat. No. 3,682,919, the catalyst of the present invention provides higher selectivity to AEEA and PIP at similar DEA conversions and ammonia/DEA mole ratios.

What is claimed is:

1. A method of making a piperazine- and aminoethylethanolamine-containing composition comprising steps of:
   (a) providing a reaction composition comprising diethanolamine; and
   (b) subjecting the reaction composition to a reductive amination in the presence of ammonia and a catalyst composition, the catalyst composition comprising a support portion and a catalyst portion, the support portion comprising an acidic mixed metal oxide comprising a transitional alumina and a second metal oxide, the catalyst portion comprising a first metal selected from the group consisting of cobalt, nickel, and copper, and a second metal selected from the group consisting of rhenium, ruthenium, rhodium, platinum, palladium, and iridium, wherein reductive amination of diethanolamine forms a product composition comprising piperazine and aminoethylethanolamine; and wherein the transitional alumina is (i) more than 50 weight percent of the alumina contained in the support and (ii) comprises a theta phase alumina, delta phase alumina, or mixtures of theta and delta phase aluminas.

2. The method of claim 1 wherein the catalyst portion is 20 wt. % or less of the catalyst composition.

3. The method of claim 1 where, in the catalyst portion, the first metal is present in an amount greater than the second metal.

4. The method of claim 1 where, in the catalyst portion, the first metal and the second metal are present in a weight ratio in the range of 10:1 to 1:1.

5. The method of claim 1 wherein the catalyst portion comprises nickel.

6. The method of claim 1 wherein the catalyst portion comprises rhenium.

7. The method of claim 1 wherein the reductive amination is carried out at a temperature of 140° C. or greater.

8. The method of claim 1 wherein diethanolamine is present at 80% wt or greater in the reaction composition.

9. The method of claim 1 where, in the product composition, aminoethylethanolamine is present in an amount (wt %) greater than piperazine.

10. The method of claim 1 where, in the product composition, the combined amount of piperazine and aminoethylethanolamine are 75% wt or greater of the products in the product composition.

11. The method of claim 1 wherein piperazine is 10-40% wt of the products in the product composition.

12. The method of claim 1 wherein the product compositions comprises reductive amination products of aminoethylethanolamine that are not piperazine or aminoethylethanolamine which are in an amount that is equal to or less than 25 wt in the product composition.

13. The method of claim 12 wherein the product compositions comprises reductive amination products of aminoethylethanolamine that are not piperazine or aminoethylethanolamine which are in an amount that is equal to or less than 10% wt in the product composition.

* * * * *